United States Patent [19]
Katz

[11] Patent Number: 5,454,817
[45] Date of Patent: Oct. 3, 1995

[54] OTO-NASAL FOREIGN BODY EXTRACTOR

[76] Inventor: David L. Katz, 465 Tom Swamp Rd., Hamden, Conn. 06518

[21] Appl. No.: 225,702

[22] Filed: Apr. 11, 1994

[51] Int. Cl.[6] .................................................. A61B 19/00
[52] U.S. Cl. ............................................ 606/106; 606/196
[58] Field of Search ................... 604/36, 37, 96, 604/185, 212, 214, 265; 606/1, 106, 190–199

[56] References Cited

U.S. PATENT DOCUMENTS

| | | | |
|---|---|---|---|
| 734,498 | 7/1903 | Bachler | 606/192 |
| 2,862,496 | 12/1958 | Hassler et al. | 604/212 |
| 4,060,080 | 11/1977 | Akiyama | 606/196 |
| 4,102,342 | 7/1978 | Akiyama et al. | 606/192 |
| 4,588,398 | 5/1986 | Daugherty et al. | 604/265 |
| 4,806,101 | 2/1989 | Rossi | 604/316 |
| 5,195,507 | 3/1993 | Bilweis | 606/1 |
| 5,196,003 | 3/1993 | Bilweis | 606/1 |
| 5,318,586 | 6/1994 | Ereren | 606/1 |

FOREIGN PATENT DOCUMENTS 2847633  5/1979  Germany .......................... 606/127

*Primary Examiner*—Stephen C. Pellegrino
*Assistant Examiner*—Glenn Dawson
*Attorney, Agent, or Firm*—Bachman & LaPointe

[57] ABSTRACT

A body passage foreign body extracting device includes an elongated flexible tubular rod having a compressible bulb attached to its proximal end. The bulb is in fluid communication with the rod in order to pump air through the rod. In addition, an inflatable balloon is attached to a distal end of the tubular rod and is in fluid communication with the rod. The balloon is positioned and connected with the rod so as to receive the air from the bulb and, as a result, become inflated. The extractor also includes a hand grip which is used for holding the extractor, compressing the bulb and maintaining compression with one hand.

13 Claims, 2 Drawing Sheets

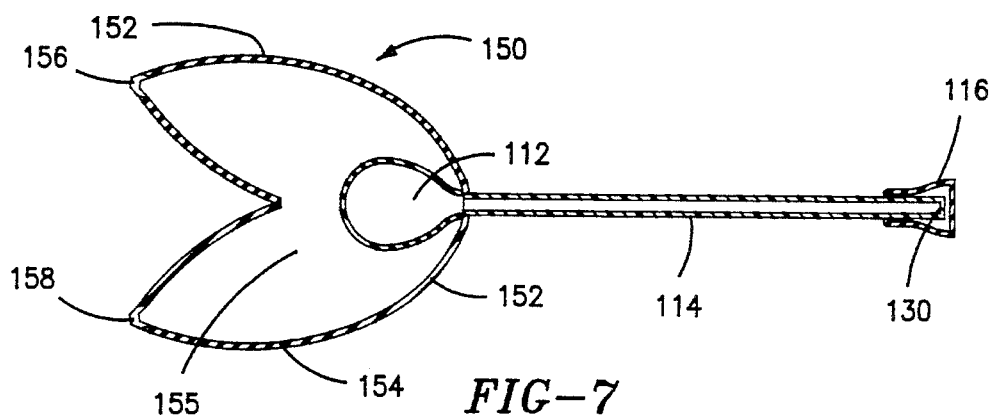
FIG-7
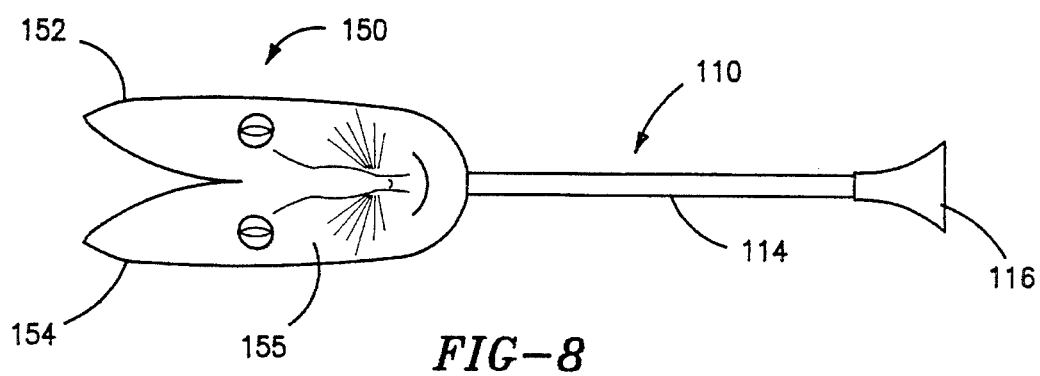
FIG-8
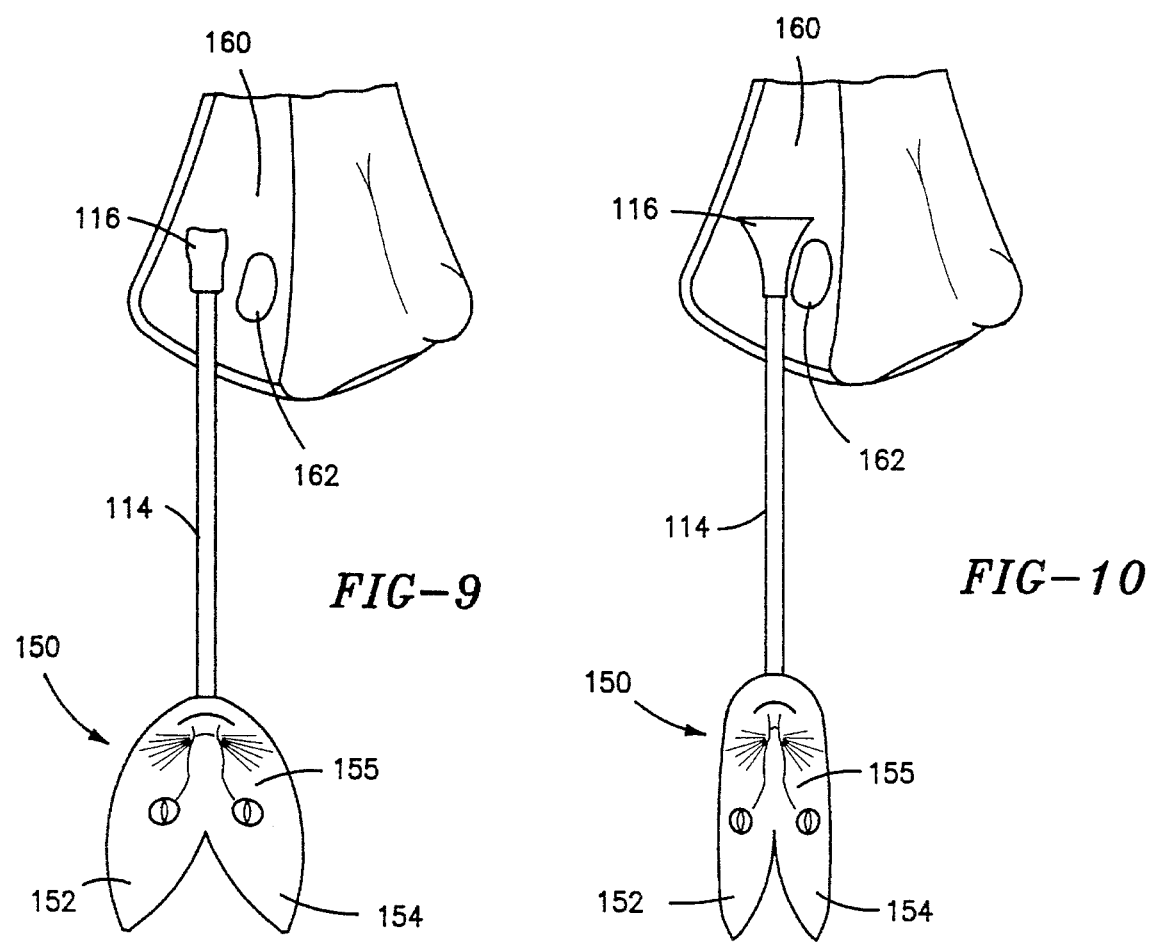
FIG-9
FIG-10

OTO-NASAL FOREIGN BODY EXTRACTOR

BACKGROUND OF THE INVENTION

The present invention is directed toward an extracting device, and more particularly, to an extracting device for removing objects from the nasal and ear passages, wherein the device may be used by physicians, other health care providers, and by laypersons as a home remedy.

Human nature leads children, and sometimes adults, to put objects where they don't belong. All too frequently, these places are a part of the human body. Nasal cavities, ear canals and throats are the most common areas into which objects are placed haphazardly or accidently lodged, causing discomfort, injury and occasionally, serious injury. Physicians frequently are visited by children having potentially dangerous foreign objects lodged in these or other places. Forceps are the most common device for removing such foreign objects from the passageway being blocked. However, forceps can be damaging to the sensitive tissues which often make up these passageways and thus, further damage may result during the attempted removal of the object. This method is often lengthy and traumatic for a child, and it may be unsuccessful, resulting in surgery.

Medical technology does include devices for removing objects from human body passages. Such devices are most frequently used for removing naturally formed stones or the like from areas such as the urinary passage. These devices are generally directed toward use with these particular passages and frequently are complex, frightening in appearance and require professional expertise and training as well as considerable and excessive manipulation and/or stabilization. These common traits of these devices are incompatible with the uses to which the instant invention are directed, i.e. toward children requiring immediate and minimally irritating and frightening attention. These devices are frequently expensive and not available for use by laypersons. Several of these devices are discussed below.

U.S. Pat. No. 4,295,464 to Shihata discloses a ureteric stone extractor with two balloon catheters. The extractor includes an inner catheter having an eccentric balloon attached to its distal end. The device also includes an outer dilatator catheter having a balloon attached to its distal end. In operation, the catheter is inserted into the ureter so that the balloon in a deflated state moves behind an object to be removed such as a stone. The balloon is then inflated and moved into contact with the object to be removed. The two balloon design of the Shihata device is more complex than necessary for the instant application, would require sedation, and would result in unnecessary discomfort to the patients. Additionally, the means of inflation and general complex appearance of the device are not conducive to reducing the escalation of anxiety in patients, particularly young patients, which frequently accompanies medical treatment. Finally, unlike the instant invention, the Shihata device would require two hands to operate as well as additional assistance to stabilize the child or other patient.

U.S. Pat. No. 4,469,100 to Hardwick is related to an extraction device for removing foreign bodies, such as a stone, lodged in a human body passage, such as a ureter. The device includes a double lumen catheter with one lumen attached to a pressure source and the second lumen attached to a suction source. A balloon surrounds the catheter and is inflated about the stone to be removed. Similar to Shihata, the Hardwick device is too complex for the instant application, requiring both a suction and pressure source whose appearance would tend to instill great anxiety in young patients. Also, the need for suction and pressure lines would make the use of the Hardwick device in homes nearly impossible and the design of the Hardwick device would also require two hands to operate.

Finally, U.S. Pat. No. 4,597,389 to Ibrahim et al. relates to a device for removing objects from tubular body passages. The device includes an elongated element having a ring at its distal end. A balloon is mounted within the ring. The balloon communicates with an air line in the tube and can be inflated after the ring has been moved about an object to be withdrawn. A syringe is used to inject air into the airline and thereby inflate the balloon. The Ibrahim device would be unacceptable for the use to which the present invention is directed in that the ring is too intrusive for use in a nasal or ear passage and the use of a syringe for inflation requires two hands for operating the device, one to hold the device and one to operate the syringe. When working with children, one hand is necessary for controlling the child where the other is necessary to control the device. Accordingly, like the other devices discussed above, without assistance, control of the patient would be lost while using the Ibrahim et al. device.

Hence, there exists a need in the medical care industry for a nasal and ear foreign body extracting device that is easy and safe to use for physicians, other health care providers, and laypersons for at home care, inexpensive to manufacture and purchase, and which is gentle to delicate tissues and gentle in appearance.

SUMMARY OF THE PRESENT INVENTION

The primary object of this invention is to provide an effective foreign body extracting device which is easily manipulated and held with one hand.

Another object of this invention is to provide a foreign object extracting device which is simple and safe to use for home care as well as physician care.

Yet another object of this invention is to provide a foreign object extracting device which is inexpensive to manufacture and purchase.

A still further object of this invention is to provide a foreign object extraction device which has an appearance which minimizes anxiety in patients, particularly young patients.

A still further object of this invention is to provide a foreign object extraction device comprised entirely of soft and gentle materials which is not traumatic to sensitive tissues comprising body passages.

An even further object of this invention is to provide a foreign object extraction device having utility in removing objects from nasal and ear passages.

The foregoing objects are attained by the inventive foreign body extracting device of the present invention which includes an elongated tubular rod, preferably comprised of a soft material, having a compressible bulb means attached to its proximal end. The bulb means is in fluid communication with the rod in order to pump air through the rod. In addition, an inflatable balloon means is attached to a distal end of the tubular rod and is in fluid communication with the rod. The balloon means is positioned and connected with the rod so as to receive the air from the bulb means and as a result, become inflated. A gripping means may also be included for more firmly holding the extracting device and compressing the bulb means with one hand.

In using the extractor of the present invention, the end of the extractor having the uninflated balloon means attached thereto is inserted into a body passage such as the nasal passage. The rod and balloon means are carefully pushed upwardly past the foreign object and because of the preferred small size, softness and flexibility of the rod, there is little danger in forcing the object upward further into the passage. At this point in the procedure, using only one hand, the bulb means is compressed once and the balloon means is inflated within the passage. While maintaining compression, the extractor is then pulled gently from the passage, causing the balloon means to engage the foreign object and drag it out of the passage thereby clearing the same.

In one embodiment of the invention, the tubular rod is a hollow catheter comprised of a soft and flexible TEFLON material. In the same embodiment, the balloon means is comprised of a latex material which upon inflation, forms a bell shaped balloon having sloping sides for engaging the foreign object. In the same embodiment, the bulb means includes a semi rigid collapsible member having a volumetric capacity which displaces enough air for inflating the balloon on one squeeze. Also, an air tight seal is formed between the catheter and the balloon and the catheter and the collapsible member.

This embodiment also includes a hand grip means for additional dexterity and control which is comprised of a semi rigid compressible member extending over and invaginating the collapsible member. The compressible member can be easily gripped and used to compress the collapsible member, hold the extractor and maintain compression with one hand.

The details of the present invention are set out in the following description and drawings wherein like reference characters depict like elements.

BRIEF DESCRIPTION OF THE DRAWINGS

FIG. 7 is a cross sectional view of the second embodiment of the extractor taken along line 7—7 of FIG. 6.

FIG. 8 is an overhead view of the second embodiment of the extractor showing the specially shaped balloon inflated, the hand grips closed and the bulb compressed.

FIG. 9 illustrates the process of inserting the extracting device into a body passage.

FIG. 10 illustrates the process of removing a foreign object from the body passage via the extracting device.

DETAILED DESCRIPTION

Figure 1:
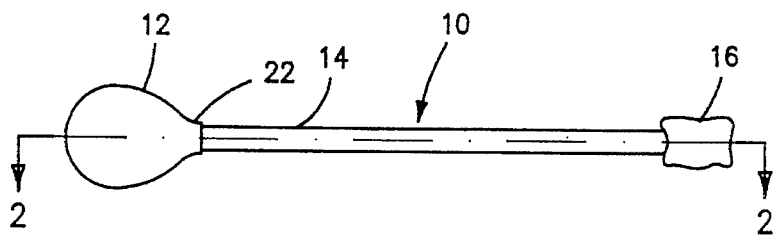
FIG. 1 is a side elevational view of an extractor in accordance with the present invention with a balloon attached to one end in an uninflated state.

Referring now to the drawings in detail, there is shown in FIG. 1 a side elevational view of the extracting device constructed in accordance with the principles designated generally as 10. As shown in FIG. 1, the extracting device generally includes a bulb 12 connected on one end to an elongated tubular rod or catheter 14, and a balloon 16 connected to the other end of the rod or catheter 14.

Referring now to the cross sectional view shown in FIG. 2, the elements of the extractor will be described in detail. The bulb 12 is used for inflating the balloon 16 with air. The bulb 12 is constructed from semi-rigid flexible rubber or similar resilient material. Accordingly, the bulb is molded or otherwise formed into a substantially egg shape configuration, being circular in frontal projection and discoid in lateral projection. The bulb comprises a shell portion 18, forming a chamber 20, and a nipple 22, for connection to the catheter 14. The bulb may also be formed by other configurations having a hollow center. The bulb 12 may be compressed by squeezing it but because of the semi-rigid yet flexible nature of the shell portion 18, it will return to the original shape after compression. The strength of the material is such that an average person may easily compress the bulb 12 with the application of a nominal squeezing force from the hand.

Figure 4:
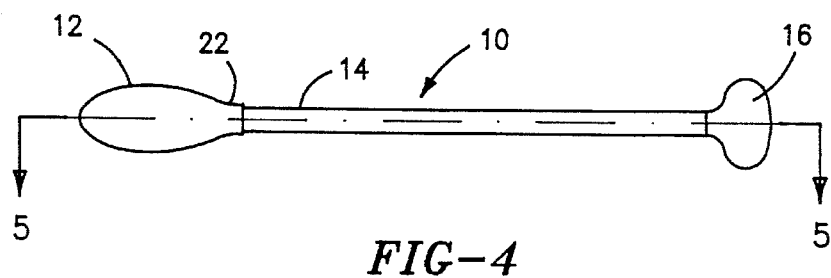
FIG. 4 is a side elevational view of the extractor with the balloon in an inflated state.
Figure 5:
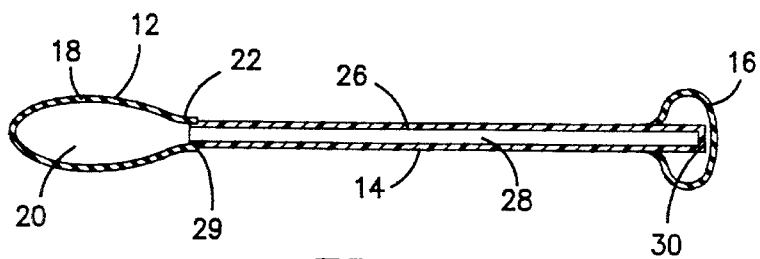
FIG. 5 is a cross sectional view of the extractor taken along line 5—5 of FIG. 4.

The volume of the chamber 20 of the bulb 12 is such that upon one compression of the bulb, the balloon will inflate to or below the maximum volume of inflation of the balloon. The volume of the bulb may be such that it displaces 2–3 cc of air when fully compressed. In order to maintain the inflation of the balloon 16, the bulb 12 must be held compressed, as illustrated in FIGS. 4 and 5. The need to hold compression acts as a safety measure for avoiding over inflation of the balloon 16. That is, if the compression is released the balloon will deflate, thus avoiding inflation of the balloon to a volume exceeding the volume of air in the bulb 12.

The bulb 12 is attached to the catheter 14 via a nipple 22. As shown in FIG. 2, the nipple 22 is formed along with the shell portion 18 during the molding process. The nipple extends outwardly from the shell portion 18 for connection to the catheter 14. The nipple 22 is also hollow, and defines an output port 24 of the bulb 12 for release of the air from the chamber 20 to the catheter 14. The nipple may be securely attached to the catheter 14 via gluing or via the elastic material comprising the nipple tightly fitting and gripping the catheter, or via any other suitable manner which causes an air tight seal between the nipple and the catheter for unrestricted flow of air from the chamber 20 to the balloon 16. In any case, the interior diameter of the nipple 22 is minimally larger than the outside diameter of the catheter 14 for causing a force fit.

Figure 2:
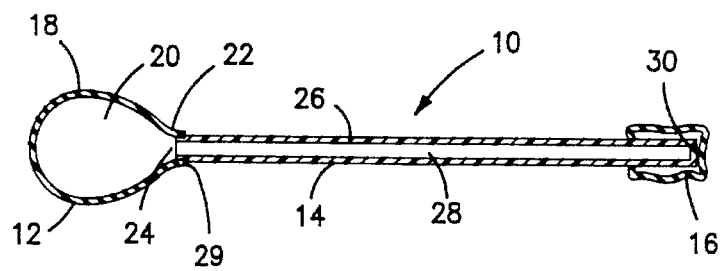
FIG. 2 is a cross sectional view of the extractor taken along line 2—2 of FIG. 1.
Figure 3:
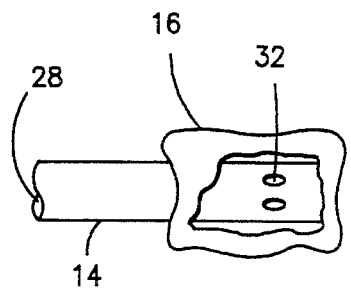
FIG. 3 is an enlarged cut away view of the balloon end of the extractor showing the uninflated balloon and catheter air holes used for inflating the balloon.

The catheter 14, referring still to FIG. 2, is tubular in shape comprising a wall 26 which encompasses the air flow passage 28. The catheter 14 is preferably constructed from 18 gauge TEFLON but other materials may be suitable. The catheter has one open end 29, which connects to the bulb nipple 22, and one closed end 30 which extends into the balloon 16. The open end 29 allows flow of air into the catheter 14 and the closed nature of the end 30 blocks flow of air out of the catheter end. However, and referring to the enlarged view of a portion of the catheter adjacent end 30 in FIG. 3, the air from the bulb exits the catheter through openings 32 which are formed through the wall 26 of the catheter 14, adjacent the closed end 30 of the catheter. As shown in FIG. 3, the openings 32 are positioned adjacent the end 30 so that while the catheter is connected to the balloon 16, the openings are inside the balloon 16. Accordingly, air from the bulb is distributed evenly within the balloon for consistently inflating the same.

Referring still to FIG. 2, the balloon 16 is preferably constructed from latex and is fused, glued or otherwise suitably attached to the catheter 14, adjacent the closed end 30 of the catheter. As discussed above, the balloon 16 is positioned adjacent the catheter end so as to envelope the openings 32. The balloon is preferably of a size to inflate to a 1 cc volume with a maximum capacity of 3 cc, upon compressing the bulb 12. Although 2–3 cc of air may be displaced upon compression of the bulb 12, due to the imperfect nature of such compression, not all of the air displaces into the balloon 16, thus allowing for a typical inflation volume of the balloon of approximately 1 cc.

Figure 6:
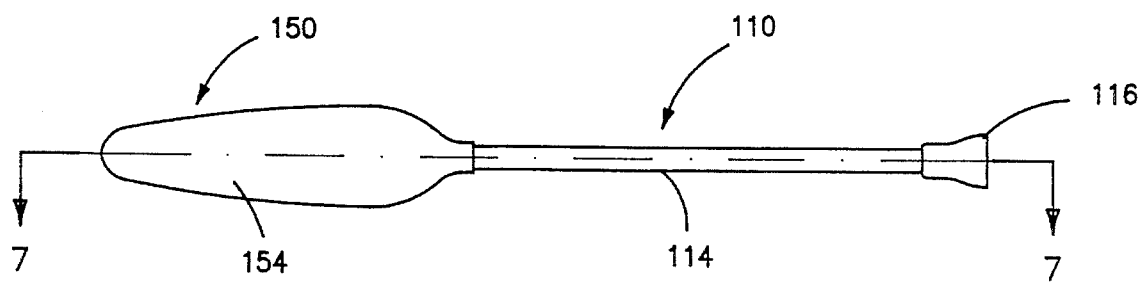
FIG. 6 is an overhead view of a second embodiment of an extractor in accordance with the present invention which includes a set of hand grips adjacent a compressible bulb and an uninflated balloon.

A second embodiment of the invention is shown in FIG. 6 wherein two elements, the bulb and the balloon are shown in altered designs. Each of these altered elements can be used alone or in combination with the remaining elements of the main embodiment. Referring to FIG. 6, the bulb 112 is substantially similar to as described above with similar volume capacities. However, the bulb includes a compressible hand grip 150 which may be molded with, or otherwise attached around the bulb 112. The compressible hand grip comprises two elongated portions 152 and 154 which extend over and invaginate the bulb 112. As shown in the cross sectional view of FIG. 7, the elongated portions 152 and 154 are also constructed from a semi-rigid rubber and are hollow, forming air chambers, and thus compressible and are connected at a central portion 155. The elongated portions preferably have an ergonomic semi-circular and elongated shape with outlet ports 156 and 158, shown in FIG. 7, for the release of displaced air upon compression of the portions to the atmosphere. To make the device 110 more gentle in appearance, the central portion 155 has a cartoon face or the like painted or otherwise formed thereon, as shown in FIG. 9.

As the elongated portions are squeezed, as shown in FIG. 8, the bulb is compressed. As the bulb becomes more compressed, the elongated portions become compressed thereby limiting the force which may be applied to the bulb via the members. Accordingly, by using the hand grip 150, the extractor 110 may be securely held and manipulated with one hand while the other hand is free to hold the patient. The bulb and hand grip assembly are attached to the catheter 114 similar to as described above and the catheter 114 is substantially identical to as described above.

Referring still to FIG. 8, the balloon 116 of the second embodiment preferably takes on a substantially bell shaped configuration upon inflation. The narrow end of the bell shaped balloon is fused to the catheter circumference adjacent to the catheter end 130, similar to as described above. As with the balloon 16, the balloon 116 is preferably formed from latex having a 1 cc preferred capacity and a 3 cc maximum capacity. The sloping sides of the balloon 116 cause the balloon to engage the object on a surface which tends to conform more gradually to the shape of the object. As with the catheter 14, the catheter 114 has openings which are located on the catheter so as to be encased within the balloon 116 and to inflate the same. The balloon 116 may be used with or without the hand grip 150.

The extractors 10 and 110 are used as described below. The main steps of the procedure are applicable to both embodiments, however, the figures illustrate the procedure with the second embodiment only. Referring to FIGS. 9 and 10, the catheter 114 with the balloon 116 fused to the closed end 130 of the catheter is inserted into a body passage 160, such as a nasal passage, having a foreign object 162 lodged therein. The catheter and balloon are manipulated past the object 162, as shown in FIG. 9. Once past the object, the bulb 112 is compressed via the hand grip 150 and the balloon 116 is inflated, as shown in FIG. 10, within the passage 160.

The extractor 110 is then removed from the passage and the balloon 116 drags the object 162 out of the passage, clearing the same. The first embodiment is used as described above except that the bulb 12 is directly compressed by the hand. The extractor of the present invention has particular utility in removing foreign objects from nasal and ear passages.

The primary advantage of this invention is that it provides an effective foreign body extracting device which is easily manipulated and held with one hand. Another advantage of this invention is that the extracting device is simple and safe to use for home care as well as physician care. An additional advantage of this invention is that the extracting device is inexpensive to manufacture and as a result thereof, inexpensive to purchase. Still another advantage of the foreign object extraction device of the present invention is that it has an appearance which minimizes anxiety in patients, particularly young patients. An even further advantage is that the foreign object extraction device of this invention has particular utility in removing objects from nasal and ear passages.

It is apparent that there has been provided in accordance with this invention a body passage foreign object extraction device which fully satisfies the objects, means, and advantages set forth hereinbefore. While the invention has been described in combination with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. A device for extracting an object from a body passage comprising:

an elongated tubular rod;

a compressible bulb means attached to a proximal end of said tubular rod and in fluid communication with said rod for pumping air through said tubular rod;

an inflatable balloon means having flexible walls configured to remove an object from the body passage attached to a distal end of said tubular rod and in fluid communication with said tubular rod for receiving said air and thereby inflating;

said balloon means adapted to be placed into the body passage and moved past said object within said body passage while in a deflated state and adapted to be inflated by said compressible bulb means when positioned behind said object so as to conform to surfaces of said body passage, engage said object and remove said object while in an inflated state upon removal from the body passage;

hand grip means positioned adjacent to and in contact with said bulb means for gripping said device and for compressing said bulb means;

said hand grip means comprising two elongated members positioned on opposite sides of said bulb means;

said elongated members adapted to be pressed inwardly against said bulb means so as to compress said bulb means; and each of said elongated members being hollow and compressible and being formed from a semi-rigid flexible material, and each of said elongated members including an air release port for releasing air upon compression of said elongated members.

2. The device according to claim 1, wherein said elongated members are integrally attached to said bulb means.

3. The device according to claim 1, wherein said balloon means has a maximum volume of inflation and said bulb means is sized to contain a volume of air sufficient to inflate said balloon means to or below said maximum volume of inflation.

4. The device according to claim 1, wherein said bulb means comprises a hollow compressible member having a definite shape, said hollow compressible member being constructed from a resilient material which causes said hollow compressible member to return to said definite shape after compression.

5. The device according to claim 1, wherein said balloon means comprises a flexible material having elastic properties which inflates into a substantially bell shaped balloon having sloping walls, said sloping walls of said balloon adapted to engage said object upon removal of said device from said body passage.

6. The device according to claim 1, wherein said tubular rod is a catheter.

7. The device according to claim 6, wherein said catheter is formed from a soft and flexible TEFLON material.

8. The device according to claim 1, wherein said tubular rod comprises an encircling wall encompassing an air flow passage, said wall having openings formed therethrough for the flow of said air from said rod and into said balloon means.

9. The device according to claim 8, wherein said rod has an open end and a closed end, said openings being located adjacent said closed end.

10. The device according to claim 1, wherein said tubular rod is soft and flexible.

11. The device according to claim 1, wherein said rod is formed from TEFLON.

12. A device for extracting an object from a body passage, comprising:

an elongated tubular rod;

a compressible bulb means attached to a proximal end of said tubular rod and in fluid communication with said rod for pumping air through said rod;

an inflatable balloon means attached to a distal end of said tubular rod and in fluid communication with said rod for receiving air and inflating; and hand grips positioned adjacent to and in contact with said bulb means for allowing the gripping of said device, said hand grips comprising two elongated members positioned on opposite sides of said bulb means, said members adapted to be pressed inwardly against said bulb means so as to compress said bulb means, wherein each of said members is hollow and compressible and formed from a semi rigid flexible material and each of said members includes an air release port for releasing air upon compression.

13. The device according to claim 12, wherein said elongated members are integrally attached to said bulb means.

* * * * *